US006468981B1

(12) United States Patent
Petros et al.

(10) Patent No.: US 6,468,981 B1
(45) Date of Patent: Oct. 22, 2002

(54) COMPOSITIONS AND METHODS FOR TARGETING PHARMACEUTICALLY ACTIVE MATERIALS TO CELLS CONTAINING ANDROGEN RECEPTORS

(75) Inventors: John Anthony Petros, Norcross, GA (US); Dennis C. Liotta, McDonough, GA (US)

(73) Assignee: Emory University, Atlanta, GA (US)

(*) Notice: Subject to any disclaimer, the term of this patent is extended or adjusted under 35 U.S.C. 154(b) by 0 days.

(21) Appl. No.: 08/283,238

(22) Filed: Jul. 29, 1994

(51) Int. Cl.⁷ ............................................. A01N 43/04
(52) U.S. Cl. ...................... 514/44; 514/12; 514/169; 424/9.1; 530/23.1; 530/23.5; 552/502; 552/509; 552/526; 552/557; 552/610; 552/638; 552/641
(58) Field of Search ........................... 514/12, 44, 169; 530/350; 536/23.1, 23.5; 424/9.1; 552/502, 509, 526, 557, 610, 641, 638

(56) References Cited

U.S. PATENT DOCUMENTS 5,166,320 A * 11/1992 Wu et al. .................... 530/395

FOREIGN PATENT DOCUMENTS

| WO | WO 91/17773  | 11/1991 |
| WO | WO 92 14493 A | 9/1992  |
| WO | WO 93/07283 A | 4/1993  |
| WO | WO 93 25197 A | 12/1993 |

OTHER PUBLICATIONS

Kaushansky et. al.; Endocrine and Repoductive Repercussions of Immunization Against Progesterone and Oestradiol in Female Rats, 1977, Acta Endocrinologica 84: 795–803.*
Rao et. al.; Synthesis of New Steriod Haptens for Radioimmunossay, 1977 Steriods, vol. 29, No. 2: 171–184.*
Stobaugh et. al.; Dihydropestosterone derivatives: relative binding affinity versus affinity purification, 1991, Steroids, vol. 56: 581–585.*
Yoshida et. al.; Prostate Camcer Metastasis–Suppressor Genes: A Current Perspective, 1998, in vivo 12: 49–58.*
Millett et. al.; Cytochrome c Is Cross–Linked to Submit II of Cytochrome c Oxidase by a Water–Soluble Carbodiimide, 1982, Biochemistry 21: 3857–3862.*
Goeij et. al.; SteriodBovine Serum Albumin Conjugates: Molecular Characterization and Their Interaction with Androgen and Estrogen Receptors, 1986, J. Steriod Biochem., vol. 24, No. 5: 1017–1031.*
Wallevik; SS–Interchanged and Oxidized Isomers of Bovine Serum Albumin Separated by Isollectric Focusing, 1976, Biochinica et Biophysica Acta420: 42–56.*
Hodgson (1995) Exp Opin Ther Patents 5:459–468.*
Miller et al (1995) FASEB J 9:190–199.*
Marshall (1995) Science 269:1050–1055.*
EF Konoplya et al (1992) Int J. Biochem 24:1979–1983.*
JC Barrett et al (1994) J Cell Biochem Suppl. 18D : 254 DBA Accession No 94–14149.*
T Ichikawa et al (1992) Cancer Research 52:3486–3490.*
Bhattacharjee et al., "Protein purification using a soluble affinity matrix; Purification of estrogen receptor with estradiol–polylysine conjugate," *Anal. Biochem.*, 1992: abstract published in *Chemical Abstracts*, vol. 116, No. 15, p. 95, abstract 144058m (1992).
Redeuilh et al., "Properties of biospecific adsorbents, obtained by immobilization of estradiol 7a–derivatives for purification of salf–uterine sytosol estradiol receptor," *Eur. J. Biochem.*, 1980: abstract published in *Biological Abstract*, vol. 70, No. 11, p. 7393, abstract 70726 (1980).
Secco et al., "2–step purification of estradiol calf uterine sytosol receptor," *C.R. Acad. Sc. Paris* 1979: abstract published in *Biological Abstract*, vol. 70, No. 11, p. 7395, abstract 70745 (1980).
Blok, L.J. et al., "Effect of testosterone deprivation on expression of the androgen receptor in rat prostate, epididymis and testis," Int. J. of Andrology (1992) 15:182–198.
Bookstein, R. et al., "Suppression of Tumorigenicity of Human Prostate Carcinoma Cells by Replacing a Mutated RB Gene," Science (1990) 247:712–715.
Bookstein, R. et al., "p53 Is Mutated in a Subset of Advanced–Stage Prostate Cancers," Cancer Res. (1993) 53:3369–3373.
Chen, P–L et al., "Genetic Mechanisms of Tumor Suppression by the Human p53 Gene," Science (1990) 250:1576–1580.
Chowdhury, N.R. et al., "Fate of DNA Targeted to the Liver by Asialoglycoprotein Receptor–mediated Endocytosis in Vivo," J. Biol. Chem. (1993) 168:11265–11271.
Coffey, D.S., "The molecular biology, endocrinology, and physiology of the prostate and seminal vesicles," In Campbell's Urology, 6th Ed. (Walsh, P.C. et al. eds.) Philadelphia, W.B. Saunders Co.) (1992) p. 242.
Curiel, D.T. et al., "Adenovirus enhancement of transferrin–polylysine–mediated gene delivery," Proc. Natl. Acad. Sci. (1991) 88:8850–8854.

(List continued on next page.)

*Primary Examiner*—James Ketter
*Assistant Examiner*—Richard Schnizer
(74) *Attorney, Agent, or Firm*—Greenlee, Winner and Sullivan, P.C.

(57) ABSTRACT

A water soluble delivery system for nucleic acids to cells having androgen receptors, preferably prostate cells, is provided comprising a steroid moiety capable of binding to said receptors, said steroid moiety being covalently linked to a polycationic material. This molecule may be complexed with therapeutic or diagnostic nucleic acids. Methods of diagnosis and therapy using these compositions are also provided, including gene therapy treatments for prostate cancer.

25 Claims, No Drawings

OTHER PUBLICATIONS

Gao, L. et al., "Direct In Vivo Gene Transfer to Airway Epithelium Employing Adenovirus–Polylysine–DNA complexes," Human Gene Therapy (1993) 4:17–24.

Harrison, R.W. et al., "Evidence for Glucocorticoid Transport Through the Target Cell Membrane," Biochem. Biophys. Res. Comm. (1974) 61:1262–1267.

Ichikawa, T. et al., "Suppression of metastasis of rat prostatic cancer by introducing human chromosome 8," Cancer Res. (1994) 54:2299–2302.

Isaacs, W.B. et al., "Wild–type p53 Suppresses Growth of Human Prostate Cancer Cells Containing Mutant p53 Alleles," Cancer Res. (1991) 51:4716–4720.

Kamb, A. et al., "A cell cycle regulator potentially involved in genesis of many tumor types," Science (1994) 264:436–440.

Liang, T.J. et al., "Targeted Transfection and Expression of Hepatitis B Viral DNA in Human Hepatoma Cells," J. Clin. Invest. (1993) 91:1241–1246.

Michael, S.L. et al. "Binding–incompetent Adenovirus Facilitates Molecular Conjugate–Mediated Gene Transfer by the Receptor–mediated Endocytosis Pathway," J. Biol. Chem. (1993) 268:6866–6869.

Nobori, T. et al., "Deletions of the cyclin–dependent kinase–4 inhibitor gene in multiple human cancers," Nature (1994) 368:753–756.

Petros, J.A. et al., "Investigation of retinoblastoma transcripts in primary prostatic adenocarcinoma," J. Urology (1991) 145:293A.

Pietras, R.J. and Szego, C.M., "Specific binding sites for oestrogen at the outer surfaces of isolated endometrial cells," Nature (1977) 265:69–72.

Steinsapir, J. and Muldoon, T.G., "Role of microsomal receptors in steroid hormone action," Steroids (1991) 56:66–71.

Veldscholte, J. et al., "Unusual specificity of the androgen receptor in the human prostate tumor cell line LNCaP: high affinity for progestagenic and estrogenic steroids," Biochimica et Biophysica Acta. (1990) 1052:187–194.

Veldscholte, J. et al., "The Androgen Receptor in LNCaP Cells Contains a Mutation in the Ligand Binding domain which Affects Steroid Binding Characteristice and Response to Antiandrogens," J. Steroid Biochem. Molec. Biol. (1992) 41:665–669.

Wagner, E. et al., "Transferrin–polycation conjugates as carriers for DNA uptake into cells," Proc. Natl. Acad. Sci. USA (1990) 87:3410–3414.

Wu, G.Y. and Wu, C.H., "Receptor–mediated in vitro gene transformation by a soluble DNA carrier," J. Biol. Chem. (1987) 262:4429–4432.

Wu, G.Y and Wu, C.W., "Receptor–mediated Gene Delivery and Expression In Vivo," J. Biol. Chem. (1988) 368:14621–14624.

Zenke, M. et al. "Receptor–mediated endocytosis of transferrin–polycation conjugates: an efficient way to introduce DNA into hematopoietic cells," Proc. Natl. Acad. Sci. USA (1990) 87:3655–3659.

* cited by examiner

COMPOSITIONS AND METHODS FOR TARGETING PHARMACEUTICALLY ACTIVE MATERIALS TO CELLS CONTAINING ANDROGEN RECEPTORS

FIELD OF THE INVENTION

This invention is in the field of chemical compounds comprising steroid and poly-L-lysine moieties. Such compounds may also be complexed with nucleic acids and are useful for targeting biologically active materials to prostate cell nuclei for example for gene therapy, or cancer therapy or diagnosis.

BACKGROUND OF THE INVENTION

Prostate cancer is the most commonly diagnosed cancer in American males, with an expected incidence of 200,000 in 1994. The projected deaths from prostate cancer are 38,000 in the same year. No curative therapy exists for advanced or metastatic prostate cancer. Chemotherapy is ineffective. Androgen ablation is palliative and non-curative. The molecular characterization of the disease has progressed very rapidly in the past few years, and it now appears that gene therapy will be the treatment of choice for advanced and metastatic disease within ten years. Several potential genetic targets of therapy exist including replacement of tumor suppressor genes, or metastasis suppressor genes, shutdown of oncogenes, and genetic induction of programmed cell death (apoptosis).

Prostate cancer is a genetically diverse disease. Some prostate cancers over-express the Ras oncoprotein, but not all. Approximately half of the prostate cancers fail to express retinoblastoma (RB) mRNA (Petros, J. A. et al. [1991], "Investigation of retinoblastoma transcripts in primary prostatic adenocarcinoma," J. Urology 145:293A; Bookstein, R., et al. [1990], "Introduction of a normal retinoblastoma gene [RB] into retinoblastoma," Science, 247:712–715). Absent or abnormal RB transcripts will result in lack of protein expression and lack of normal regulation of cell cycle.

Some prostate cancers show the common p53 promoter mutation (Bookstein, R. et al. [1993], "p53 is mutated in a subset of advanced-stage prostate cancers," Cancer Res. 53:3369–3373), but most do not. This genetic diversity is consistent with the well-accepted "multi-hit" theory of solid tumor oncogenesis, and is responsible for the varied clinical manifestations of the disease. This genetic diversity is also responsible for the hormonal responsiveness of some tumors and the hormonal resistance of others.

Correction of mutant RB or p53 stops tumor growth. The RB gene was shown to be mutant in a prostate cancer cell line, and the transfection of wild-type RB shown to abrogate tumorigenicity in nude mice (Bookstein, R., et al. [1990], "Suppression of Tumorigenicity of Human Prostate Carcinoma Cells by Rephasing a Mutated RB Gene" Science, 247:712–715) and in human tumor cells. (Chen, P-L, et al. [1990], "Genetic Mechanisms of Tumor Suppression by the Human p53 Gene," Science 250:1576–1580). Subsequent reports which indicated that this was an uncommon event in primary human tumors (Isaacs, W. B., et al. [1991], "Wild-type p53 suppresses growth of human prostate cancer cells containing mutant p53 alleles," Cancer Res. 51:4716–4720) were flawed in assaying for only one mutation. Studies in our laboratories have demonstrated that in fact up to fifty percent of tumors fail to make normal RB transcripts (Petros, J. A. et al. [1991], "Investigation of retinoblastoma transcripts in primary prostatic adenocarcinoma," J. Urology 145:293A), and it is likely that an even greater percentage will be shown to be abnormal when large numbers of tumors have been assayed for protein expression. Similarly, p53 has been shown to be mutated in twenty to twenty-five percent of advanced-stage prostate cancers (Bookstein, R. et al. (1993), "p53 is mutated in a subset of advanced-stage prostate cancers," Cancer Res. 53:3369–3373), but relatively few early stage prostate cancers. The reintroduction of p53 into cell lines with mutant p53 abolished their ability to grow and divide (Isaacs, W. B., et al. [1991], "Wild-type p53 suppresses growth of human prostate cancer cells containing mutant p53 alleles," Cancer Res. 51:4716–4720).

A further tumor suppressor gene is p16 (also known as Multiple Tumor Suppressor 1 (MTS1), which encodes the p16 inhibitor of cyclin-dependent kinase 4 (Kamb, A., et al. [1994], "A cell cycle regulator potentially involved in genesis of many tumor types," Science 264 436–440; Nobori, T., et al. [1994], "Deletions of the cyclin-dependent kinase-4 inhibitor gene in multiple human cancers," Nature 368:753–756). DNA encoding genes for suppression of metastasis of prostate cancer is also known to the art, and has been used via microcell-mediated chromosome transfer to suppress metastatic ability of microcell hybrids (Ichikawa, T., et al., "Suppression of metastasis of rat prostatic cancer by introducing human chromosome 8," Cancer Res. 54:2299–2302).

Polylysine DNA complexes have been used to transfer genes into cells in vitro (Curiel, D. T., et al. (1991), "Adenovirus enhancement of transferrin-polylysine-mediated gene delivery," Proc. Natl. Acad. Sci. USA 88:8850–8854; PCT application PCT/EP92/02234 for "Composition for Introducing Nucleic Acid Complexes Into Higher Eukaryotic Cells," claiming priority to U.S. application Ser. No. 07/937, 788 to Curiel, et al. filed Sep. 2, 1992, which is fully incorporated herein by reference) and in vivo (Gao, L., et al. [1993], "Direct In Vivo Gene Transfer to Airway Epithelium Employing Adenovirus-polylysine-DNA complexes," Human Gene Therapy 4:17–24).

The surface receptor for asialoorosomucoid has been found to mediate DNA uptake in hepaitocytes. A soluble DNA carrier system consisting of an asialoglycoprotein linked to poly-L-lysine has been used to bind DNA and hepatitis B virus DNA constructs to liver cells. Liver cells express specific surface receptors for asialoorosomucoid. Covalent linkage of asialoorosomucoid with poly-L-lysine followed by ionic bonding with DNA creates a soluble delivery system (Wu, G. Y. and Wu, C. H. [1987], "Receptor-mediated in vitro gene transformation by a soluble DNA carrier," J. Biol. Chem. 262:4429–4432). The same asialoorosomucoid-poly-L-lysine-DNA construct has been used to selectively transform the liver in vivo in a rat model. (Wu, G. Y. and Wu, C. W. [1988], "Receptor-mediated Gene Delivery and Expression in Vivo," J. Biol. Chem. 368:14621–14624). Transformation of asialoglycoprotein receptor-positive human hepatoma cells with this system has also has also been shown. (Liang T. J., et al. [1993], "Targeted transfection and expression of hepatitis B viral DNA in human hepatoma cells," J. Clin. Invest. 91:1241–1246). Using this receptor-mediated delivery and targeting system it has been possible to induce production of proteins encoded for by the DNA so introduced. This has been shown to be receptor mediated since competitive binding with non-linked asialoorosomucoid abrogated the expression. In addition, receptor-negative cells do not take up the DNA or express the proteins. After intravenous injection, DNA complexed with asialoglycoprotein-polylysine conjugates is expressed transiently. Cytoplasmic vesicles are the main site of persistence of endocytosed DNA (Chowdhury, N. R., et al. [1993], "Fate of DNA Targeted to the Liver by Asialoglycoprotein Receptor-mediated Endocytosis in Vivo," J. Biol. Chem. 268:11265–11271).

Transferrin-polycation complexes (transferrin-polylysine and transferrin-protamine) have been used to transfer reporter genes into hematopoietic cells (Zenke, M., et al. [1990], "Receptor-mediated endocytosis of transferrin-polycation conjugates: an efficient way to introduce DNA into hematopoietic cells," Proc. Natl. Acad. Sci. U S A, 87:3655–3659; Wagner, et al. [1990], "Transferrin-polycation conjugates as carriers for DNA uptake into cells," Proc. Natl. Acad. Sci. U S A 87:3410–3414). (A transferrin-poly-L-lysine is commercially available as hT fpL/AdpL of Serva Biochemical and was used in combination with antibody-bound adenovirus to improve efficiency of endocytosis in HeLa cells in culture (Michael, S. L. et al., [1993] "Binding-incompetent Adenovirus Facilitates Molecular Conjugate-Mediated Gene Transfer by the Receptor-mediated Endocytosis Pathway," J. Biol. Chem. 268:6866–6869).

PCT Application WO 91/177 3 published November 28, 1991 to Boehringer Ingelheim, incorporated herein by reference, relates to a system for transporting nucleic acids with a specific activity for T-cells. This system makes use of cell surface proteins of the T-cell lineage, e.g. CD4, the receptor used by the HIV virus. The nucleic acid to be imported is complexed with a protein-polycation conjugate, the protein component of which, i.e. the recognition domain, is a protein capable of binding to the T-cell surface protein, e.g. CD4, and cells which express this surface protein are brought into contact with the resulting protein-polycation/nucleic acid complexes. It has been shown that DNA transported into the cell by means of this system is expressed in the cell.

Steroid hormones interact with components of biological membranes and may enter their respective target cells by diffusion or by a membrane-mediated process which is saturable and temperature-dependent (Pietras, R. J. and Szego, C. M. [1977], "Specific binding sites for oestrogen at the outer surfaces of isolated endometrial cells," Nature 265:69–72). The subcellular distribution of steroid receptors in target tissues is still a controversial issue. Little information has been gathered concerning the nature and properties of membrane-bound steroid receptors. Plasma membranes of target cells may contain steroid receptors (Steinsapir, J. and Muldoon, T. G. [1991], "Role of microsomal receptors in steroid hormone action," Steroids 56:66–71).

The human androgen receptor has been characterized and consists of a protein comprising 917 amino acids having three domains that regulate transcription, DNA binding, and steroid specificity (Coffey, O. S. [1992], "The molecular biology, endocrinology, and physiology of the prostate and seminal vesicles," In Campbell's Urology, 6th Ed [Walsh, P. C. et al. eds.] Philadelphia, W. B. Saunders Co., p. 242). The androgen receptor may be found in prostate tissue, metastatic cancerous prostate tissue, hair follicles, muscle, and skin. Androgen receptors are cytoplasmic but may also be located in the cell membrane. A specific mechanism, associated with the cell membrane, must transport steroids into the target cell before they can bind to the cytosolic receptor (Harrison, R. W., et al. [1974], "Evidence for Glucocorticoid Transport through the Target Cell Membrane," Biochem. Biophys. Res. Comm. 61:1262–1267).

Androgen receptors have affinity for a number of androgens and other steroids. Prostate tumor cells have affinity for progestagenic and estrogenic steroids (Veldscholte, J., et al. [1990], "Unusual specificity of the androgen receptor in the human prostate tumor cell line LNCaP: high affinity for progestagenic and estrogenic steroids," Biochimica et Biophysica Acta. 1052:187–194). Such tumor cells also have affinity to antiandrogens such as cyproterone acetate (Veldscholte, J., et al. [1992], "The Androgen Receptor in LNCaP Cells Contains a Mutation in the Ligand Binding Domain which Affects Steroid Binding Characteristics and Response to Antiandrogens," J. Steroid Biochem. Molec. Biol. 41:665–669). Androgen deprivation results in increased expression of the androgen receptor. Fourfold increase in androgen receptor mRNA in the prostate followed medical castration or rats (Blok, L. J., et al. [1992], "Effect of testosterone deprivation on expression of the androgen receptor in rat prostate, epididymis and testis," Int. J. of Andrology 15:182–198).

Effective gene therapy for metastatic disease depends upon delivery of a high concentration of the therapeutic agent to the sites of metastases. This delivery is difficult with respect to prostate tissue because of the plasma solubility requirements of agents. Uptake of therapeutic agents by prostate tissue has generally been thought to require lipophilic carriers.

There is a need for an efficient water-soluble system for introducing nucleic acid into androgen receptor-containing cells, especially prostate cells and metastatic prostate cells, especially for purposes of gene therapy and cancer therapy.

SUMMARY OF THE INVENTION

This invention provides a water-soluble delivery system for nucleic acids to cells having androgen receptors, preferably prostate cells, including cancerous or metastatic prostate cells. The invention includes a compound comprising a steroid moiety capable of binding to an androgen receptor, said steroid moiety being covalently linked to a polycationic salt. This compound is useful for complexing with nucleic acids desired to be delivered to the cells. The compounds are useful for gene therapy, cancer therapy, and diagnosis. The use of a moiety for which the androgen receptor has affinity enables targeting of injectable materials to prostate and other androgen receptor-containing cells. Such injectable materials must be water-soluble (serum-soluble). Previously it has been believed that compounds must be provided in lipophilic carriers in order to be taken up by prostate cells.

Many steroid moieties are capable of binding to androgen receptors including androgens, estrogens, synthetic androgens and estrogens, antiandrogens, metabolically altered analogs of the foregoing, and others, all as known to the art.

Polycationic salts useful for completing with nucleic acids include salts of cationic polyamines such polylysines, specifically poly-L-lysines, polyarginines, specifically poly-L-arginine, polyhistidine, and protamines.

The counter-ion of such salts can be any pharmaceutically acceptable ion, preferably a halogen ion, and most preferably bromide.

This invention also provides a method for expressing a protein in a cell containing androgen receptors comprising contacting said cell with a nucleic acid complex of a compound comprising a steroid moiety capable of binding to an androgen receptor of said prostate cell, the steroid moiety being covalently linked to a polycationic salt having a pharmaceutically acceptable counterion, wherein said nucleic acid encodes said protein, whereby said protein is detectably expressed in said cell. Preferably said prostate cell is a cancerous cell, which term includes metastatic prostate cells not localized to the prostate.

A method is also provided for targeting a biologically active material to the nucleus of a cell containing an androgen receptor comprising contacting said cell with a composition comprising said biologically active material covalently or ionically bonded to a compound comprising a steroid moiety covalently linked to a polycationic material whereby said biologically active material is delivered to the nucleus of said cell.

When the foregoing methods comprise injecting the complex into a suitable host, dosages in the range of from about 5 mg to about 250 mg DNA complexed with about 5 to about 10 mg steroid/polycationic compound are suitable.

This invention also provides a method for detecting the location of androgen-receptor containing cells in a subject comprising injecting into said subject a pharmaceutically effective amount of a nucleic acid complex of a compound comprising a steroid moiety capable of binding to an androgen receptor of said prostate cell, said steroid moiety being covalently linked to a polycationic salt having a pharmaceutically acceptable counterion, wherein said nucleic acid comprises detectably labelled nucleic acid. Dosages in the range of from about 5 mg to about 250 mg DNA completed with about 5 to about 10 mg steroid/polycationic compound are suitable for diagnosis and are capable of identifying the sites of metastatic tissue.

DETAILED DESCRIPTION OF THE PREFERRED EMBODIMENT

This invention involves the use of compounds containing steroids capable of binding to androgen receptors for targeting therapeutic or diagnostic molecules to prostate cells and other cells containing androgen receptors. Such therapeutic compounds are used for gene therapy and for treatment of prostate cancers. Diagnostic molecules include radiolabelled nucleic acids to diagnose metastatic prostate cancer sites.

Steroids have the following general structure:

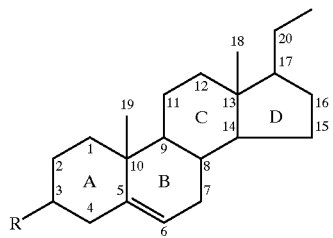

R is generally O or OH. A line above C-10 or C-13 denotes a methyl group. Substituents above the plane are termed beta- oriented and shown by a solid bond. In contrast, a substituent that is below the plane is alpha-oriented and denoted by a dashed line. A hydrogen atom attached to C-5 can be alpha or beta-oriented. When this hydrogen atom is alpha-oriented, the A and B rings are fused in a trans conformation, whereas a beta-orientation yields a cis fusion. The absence of a symbol for the C-5 hydrogen atom implies a trans fusion. The C-5 hydrogen atom is alpha-oriented in all naturally-occurring steroid hormones that contain a hydrogen atom in that position. A trans fusion yields a nearly planar structure, whereas a cis fusion gives a buckled structure.

Preferably the steroid moiety contains unsaturation in the A and/or B rings and has a substantially planar structure.

Some steroid moieties which bind to androgen receptors and are suitable for use in the compounds of this invention are: dihydrotestosterone, testosterone, estradiol, progesterone, androstanediol, androstenedione, hydroxyandrostenedione, mibolerone, cortisol, methyltrienolone, promegestone, triamcinolone acetonide, cyproterone acetate, hydroxyflutamide, nilutamide, casodex, tamoxifen, and 17β-hydroxy-17α-methyl-estra-4,9,11-trien-3-one (R1881). Most preferably the steroid moiety is dihydrotestosterone. Relative binding affinities of several steroids for the androgen receptor of LNCaP prostate tumor cells are given by Veldscholte, J. et al. (1990), "Unusual specificity of the androgen receptor in the human estrogenic steroids," Biochemica et Biophysica Acta, 1052:187–194, as follows:

| R1881 | 100 |
|---|---|
| Dihydrotestosterone | 88 |
| Testosterone | 25 |
| Progesterone | 17 |
| Estradiol | 2.4 |

The polycationic material is covalently bonded to the steroid moiety at a site which does not interfere with binding of the molecule to an androgen receptor. Preferably, the polycationic material is attached at C-20. The covalent bond may be any covalent bond known to the art. Preferably the linkage is an ester bond formed by condensation of a C-20 alcohol with a carboxyl moiety of said polycationic material. More preferably, the linkage is an amide linkage formed by condensation of a C-20 amine with a carboxyl moiety of said polycationic material, or a disulfide bond.

The polycationic material is preferably poly-L-lysine, and may be of any molecular weight range. The invention is exemplified using a poly-L-lysine of 59 kD to complex with 7.4 kb of DNA. However, as will be appreciated by those skilled in the art, any size polycationic material may be used provided the molecule is of sufficient size to complex the desired nucleic acid. The charge of the polycationic material may also be adjusted to ensure complexing of the desired nucleic acid. The complexing may be done as exemplified herein or by any means known to the art.

A preferred embodiment is a dihydrotestosterone moiety covalently linked via an ester linkage to poly-L-lysine hydrobromide of the following formula:

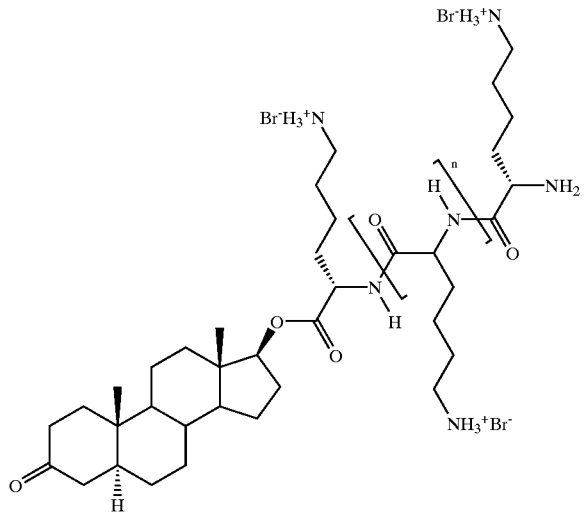

"n" can be any number greater than zero and preferably equals about 100 to about 1,000, and more preferably equals about 500 to about 600.

In a preferred embodiment, the steroid/polycationic compound of this invention is complexed with nucleic acid. The nucleic acid is preferably one which is capable of therapeutically modifying or locating a prostate cell. The prostate cell may be normal or abnormal, e.g. may be a tumor or metastatic cell, or a normal prostate cell. Preferably the nucleic acid is DNA, as it is less resistant to degradation than RNA when injected.

As will be readily appreciated by those skilled in the art, the complex can also contain other moieties such as adenovirus and adenovirus antibody sequences to aid endocytosis and help prevent degradation. Liposomes may also be used as part of the delivery systems of this invention.

This androgen receptor mediated delivery system, i.e., the steroid/polycationic molecule of this invention, targets therapeutic or diagnostic material to the nucleus as the specific subcellular site and therefore overcomes previous problems with trapping the material in non-nuclear locations.

The nucleic acid complexes of this invention are useful for gene therapy for prostate cancer. This may be accomplished by targeting a normal tumor or metastasis suppressor gene to a prostate cell lacking the normal suppressor gene. Suitable suppressor genes for this purpose are retinoblastoma (RB), p53, p16, and prostate cancer metastasis suppressor, all known to the art as discussed above. Preferably the suppressor gene is RB or p53.

Over-expression of the Ras gene is also a defect which may be corrected by gene therapy, such as by complexing inhibitors such as antisense DNA to the gene or promoter to the targeting compound.

Nucleic acids as therapeutically effective substances can also be used to inhibit specific cell functions, e.g. antisense RNAs and DNAs have proved effective in the selective inhibition of specific gene sequences. Their mode of activity enables them to be used as therapeutic agents for blocking the expression of certain genes (such as deregulated oncogenes or viral genes) in vivo. When the nucleic acid complexes of this invention contain prostate-specific antigens, antisense DNA inhibiting regulation and growth of normal cells can also be included in the complexes.

As not all prostate cancers have defects in suppressor genes, any highly successful therapeutic protocol for advanced prostate cancer must take this into account. Therapy must be individualized, and based on a meticulous characterization of each patient's cancer, its genetic composition, and phenotypic behavior. This is particularly true for strategies involving gene therapy. It does no good to transfect the RB or p53 cDNA into a patient or tumor which expresses these genes normally. It does no good to produce cytokines around a tumor which has developed antigenic diversity or disguise and will therefore be unrecognized by the immuno-effector cells called to the site. It would be of little benefit to block the action of the Ras oncoprotein if RAS over-expression is not taking place in that particular cell. Methods for characterization of cancers are as known to the art and as described herein.

In the method of this invention for expressing a protein in a cell containing androgen receptors, the cell, which may be normal or cancerous, is contacted with a nucleic acid complex, preferably a DNA complex, of a compound comprising a steroid moiety capable of binding to an androgen receptor of said cell, said steroid moiety being covalently linked to a polycationic salt having a pharmaceutically acceptable counterion. The protein is detectably expressed in the cell. Expression is detected by means known to the art, e.g. as described herein.

Preferably a subject in whom expression is desired is treated with the nucleic acid complexes of this invention by injection of a water-soluble preparation of a complex containing DNA encoding a therapeutic protein as discussed above. Suitable pharmaceutical carriers for such injections include normal saline, 5% glucose, and other carriers known to the art.

The treatments of this invention are especially useful for patients who have been treated by androgen ablation since androgen deprivation increases the transcription, number and receptivity of the patient's androgen receptors.

When the complexes of this invention are used for diagnosis, they comprise DNA or other substances labelled so as to be detectable in diagnostic methods, e.g. by radiolabelling, such as with Tc99. The presence of the radio-labelled substances is detected using radiation detectors known to the art. The presence of such substances in tissue such as kidney tissue, lung tissue, etc. not normally having androgen receptors indicates the presence of metastatic sites.

EXAMPLES

Example 1

Preparation of DHT-poly-L-lysine HBr

A mixture of poly-L-lysine HBr (54.1 mg, $1.004 \times 10^6$ mol; Mw: 53,900, P-2636, Sigma: Lot #14H-5537), 1-ethyl-3-(3-dimethylaminopropyl)carbodiimide-HCl (EDAC) ($2.19 \times 10^6$ mol) and dihydrotestosterone (DHT) ($2.134 \times 10-6$ mol) in a solvent mixture consisting of acetonitrile (3mL), DMF (5mL), $NEt_3$ (1 mL) and water (5 mL) was stirred at room temperature for 2 d. The solvents were removed under vacuum. The desired compound was separated by size exclusion chromatography. Part of the sample was also purified by dialysis. EDAC solution was prepared by dissolving EDAC (2.1 mg) in 10 mL of acetonitrile ($1.095 \times 10^{-3}$M). DHT solution was prepared by dissolving DHT (3.1 mg) in 10 mL of acetonitrile ($1.067 \times 10^{-3}$M).

Example 2

Preparation of DHT-poly-L-lysine-DNA Complex.

DHT poly-L-lysine as described in Example 1 was dialyzed against tris-EDTA buffer pH=7 ("HMW-D") or purified by gel filtration column chromatography ("HMW-2= fraction #2 of the column, HMW-9=fraction 9 of the column). Protein concentrations of reaction products and column fractions were determined by the coomassie blue method. DHT-poly-L-lysine at amounts from 0.05 micrograms to 12.5 micrograms were mixed with pCMV-beta DNA expression construct containing the lacZ gene driven by the CMV immediate early promoter/enhancer in a pVC19 backbone, in amounts from 3 to 50 micrograms in 100 microliters of water at room temperature for one hour with vortex mixing every 15 minutes.

Example 3

Expression of DNA in Prostate Cell Nuclei

The reaction products of Example 2 were added to 1–3 ml of tissue culture media supplemented with 10% fetal bovine serum and filtered through 0.2 micron filter and added to subconfluent cultures of LNCaP cells growing on glass slides. Cells were incubated at 37 degrees C. 5% $CO_2$ for 48 hours. Next, adherent cells were washed with phosphate buffered saline (PBS) and fixed with 2% paraformaldelyde in 0.1 M NaPO$_4$ buffer pH=7.4 for 45 min. to one hour. Fixative was aspirated and cells rinsed with PBS and X-gal stain was applied. Cells were incubated with stain for 12 hours at 37 degrees C. and examined under the microscope for blue staining indicative of transformation and expression of DNA so introduced. Each culture plate was scored for the number of cells which turned blue.

Cells transfected by electroporation stained positive (positive control for staining and integrity of the expression construct); cells treated with saline or DHT-poly-L-lysine alone, or 7.2 micrograms (mcg) of DNA alone showed no positive cells. Cells treated with HMW-D 0.05 mcg combined with 3.6 mcg DNA had a single transfected cell, as did culture treated with HMW-9 0.05 mcg plus 3.6 mcg DNA. Culture with HMW-9 0.05 mcg plus 7.2 mcg DNA had two transformed cells.

Four cultures treated with HMW-D and DNA at various proportions in concentrations described in Example 2 had 16 transformed cells, with optimal transformation at 0.2 mcg HMW-D plus 3.6 mcg DNA (pCMV-beta); 6 cultures of HMW-2 plus DNA had 9 transformed cells, with optimal transformation at 12.5 mcg HMW-2 plus 50.4 mcg DNA; and 5 cultures of cells treated with various proportions of HMW-9 and DNA had 19 transformed cells with optimal transformation at 0.2 mcg HMW-9 50.4 plus mcg DNA. Negative controls were all negative; positive controls were all positive; and a single culture plate treated with 3.2 mcg DNA had a single transformed cell. The constructs of this invention have been shown to be capable of delivering at least 7.4 kb of DNA to the nucleus of LNCaP cells. DNA alone is incapable of transforming the cells. Following transformation, the DNA was intact and capable of transcription and translation of functional enzyme product.

Example 4

Molecular Characterization of Tumors.

Tumors removed at the time of radical prostatectomy or upon excision of metastatic site are divided into two samples, one kept moist in saline soaked gauze for xenografting, the other minced and frozen in liquid nitrogen in the operating room. Microscopic dissection of 6 micron thick frozen sections is carried out in order to obtain pure tumor for further characterization. Sequence analysis of p53 gene allows determination of degree of mutation (Isaacs, W. B., et al. [1991]), "Wild-type p53 suppresses growth of human prostate cancer cells containing mutant p53 alleles," Cancer Res. 51:4716–4720). Sequence analysis of p16 similarly allows determination of degree of mutation (Nobori, T. et al. [1994], "Deletions of the cyclin-dependent kinase-4 inhibitor gene in multiple human cancers," Nature 368:753–756). Northern blot analysis and quantitative RT/PCR shows the level of RB expression (Petros, J. A. and Catalona, W. J. [1991], "Investigation of retinoblastoma transcripts in primary prostatic adenocarcinoma," Urology 145:293A).

Example 5

Development of Hormone-Resistant and Metastatic Human Prostate Cancer Cell Line

A new cell line derived from parent line PC3 (American Tissue Culture) was developed by four serial passages between tissue culture flasks and nudemice and designated PC3-N4. This has been characterized and found to be hormonally resistant and metastatic in nude mice. Injection of 500,000 or more cells produces metastases in 100% of animals within 4–6 weeks and most mice are dead within 8 weeks. The cell line is androgen insensitive.

Example 6

Expression of Tumor Suppressor Genes

Tumor suppressor gene constructs are created using tumor suppressor genes p53, RB, p16 and prostate cancer metastasis suppressor gene behind a cytomegalovirus (CMV) promoter-enhancer complexed with DOTMA:DIPE (1:1) liposomes, and injected intravenously in nude mice infected with human prostate cancer cell line PC3-N4. Expression of tumor suppressor genes is found using monoclonal anti-p53, anti p16 and anti-RB, and anti-prostate cancer metastasis suppressor antibodies.

Example 7

Integration and Expression of Tumor Suppressor Genes in Vitro and in Vivo

Androgen receptor positive cell lines LnCaP, and DU-145A, and androgen receptor negative cell lines PC3N-4, 9479 and DU-145B are used to show integration and expression of tumor suppressor genes. The DU-145A and DU-145B cell lines are a pair of androgen receptor positive and negative cell lines which are negative for retinoblastoma expression. After treatment with the tumor suppressor gene/ CMV promoter-enhancer constructs of RB complexed with DHT-poly-L-lysine by the procedure of Example 2, cells are assayed for DNA integration by southern analysis, transcription by northern analysis, and protein production by western blot. Each of these cell lines is propagated as solid tumors in nude mice and used to show successful targeting and integration of the soluble complexes into androgen-receptor positive, retinoblastoma negative cells and conversion of these cells to retinoblastoma positive cells. Primary and metastatic sites are then assayed by PCR amplification of human specific retinoblastoma (RB) and CMV sequences. Immunohistochemical analysis with monoclonal anti-human-RB antibodies is used to detect expression of human RB protein. Necropsy and DNA, RNA and protein expression show organ specificity and longitudinal studies are used to show stability of integration and expression. The integration and expression of p53, p16 and prostate cancer metastasis suppressor is similarly shown using cell lines which are androgen receptor positive and negative and negative for these suppressor genes.

Example 8

Treatment of Metastatic Prostate Cancer Cells.

Suppressor gene/CMV promoter-enhancer constructs of p53, RB, p16 and prostate cancer metastasis suppressor are complexed with DHT-poly-L-lysine by the procedure of Example 2 and intravenously administered to human subjects diagnosed with metastatic prostate cancer having mutated p53, p16 or RB tumor suppressor genes or mutated prostate cancer metastasis suppressor genes, at a range of dosages from 5 mg to 250 mg DNA complexed with 5–10 mg DHT-poly-L-lysine.

Example 9

100 mg of synthetic poly-AC-nucleotide labelled with Tc99 of approximately 7 kb is complexed with 5 mg DHT-poly-L lysine of Example 2 by the method of Example 3 and solubilized in normal saline for injection into a patient. After 24 hours the sites of radioactive concentration are detected by means of a radiation detection scanner and compared with the pattern of such sites in healthy individuals. Prostate cancer metastatic sites are detected by this means.

As will be appreciated by those skilled in the art, the foregoing examples are illustrative only and not meant to limit the scope of this invention which is defined by the appended claims and by equivalents to the claimed embodiments which would be obvious to one skilled in the art in view of the teachings herein.

What is claimed is:

1. A compound comprising a steroid moiety capable of binding to an androgen receptor, said steroid moiety being covalently linked to a polycationic salt complexed with nucleic acid capable of therapeutically modifying or revealing the presence of an androgen-receptor-containing cell.

2. The compound of claim 1 wherein said steroid moiety is selected from the group consisting of dihydrotestosterone, testosterone, estradiol, progesterone, androstanediol, androstenedione, hydroxyandrostenedione, mibolerone, cortisol, methyl nenolone, promegestone, triamcinolone acetonide, cyproterone acetate, hydroxyflutamide, nilutamide, casodex, 17β-hydroxy-17α-methyl-estra-4,9,11-trien-3-one, and tamoxifen.

3. The compound of claim 1 wherein said steroid moiety is dihydrotestosterone.

4. The compound of claim 1 wherein said steroid moiety is testosterone.

5. The compound of claim 1 wherein said steroid moiety is estradiol.

6. The compound of claim 1 wherein said steroid moiety is mibolerone.

7. The compound of claim 1 wherein said steroid moiety is progesterone.

8. The compound of claim 1 wherein the A and B rings of said steroid moiety have a trans fusion.

9. The compound of claim 1 wherein the A and/or B rings of said steroid moiety contain unsaturation.

10. The compound of claim 1 wherein said covalent linkage is an ester linkage.

11. The compound of claim 1 wherein said covalent linkage is an amide linkage.

12. A compound comprising a steroid moiety capable of binding to an androgen receptor, said steroid moiety being covalently linked to a polycationic salt wherein said covalent linkage is at position 20 of said steroid moiety.

13. The compound of claim 1 wherein said polycation is poly-L-lysine.

14. A The compound of claim 1 wherein said polycationic salt is a poly-L-lysine halogen salt.

15. A compound comprising a steroid moiety capable of binding to an androgen receptor, said steroid moiety being covalently linked to a polycationic salt wherein said polycationic salt is polylysine bromide.

16. A pharmaceutical preparation in injectable form useful for the treatment of prostate cancer comprising a compound comprising a dihydrotestosterone moiety covalently linked via an amide linkage with poly-L-lysine complexed with DNA encoding p53 in a suitable pharmaceutical carrier.

17. A pharmaceutical preparation in injectable form useful for the treatment of prostate cancer comprising a compound comprising a dihydrotestosterone moiety covalently linked via an amide with poly-L-lysine complexed with DNA encoding RB in a suitable pharmaceutical carrier.

18. A pharmaceutical preparation in injectable form useful for the treatment of prostate cancer comprising a compound comprising a dihydrotestosterone moiety covalently linked via an amide linkage with poly-L-lysine complexed with DNA encoding p16 in a suitable pharmaceutical carrier.

19. A method for expressing a protein in a cell containing androgen receptors comprising contacting said cell with a nucleic acid complex of a compound comprising a steroid moiety capable of binding to an androgen receptor of said cell, said steroid moiety being covalently linked to a polycationic salt having a pharmaceutically acceptable counterion, wherein said nucleic acid encodes said protein, whereby said protein is detectably expressed in said cell.

20. The method of claim 19 wherein said cell is a cancerous prostate cell.

21. A method for targeting a biologically active material to the nucleus of a cell containing an androgen receptor comprising contacting said cell with a composition comprising said biologically active material covalently or ionically bonded to a compound comprising a steroid moiety capable of binding to an androgen receptor of said cell, said steroid moiety being covalently linked to a polycationic salt having a pharmaceutically acceptable counterion, whereby said biologically active material is delivered to the nucleus of said cell.

22. A method for detecting the location of androgen-receptor-containing cells in a subject comprising injecting into said subject a pharmaceutically effective amount of a nucleic acid complex of a compound comprising a steroid moiety capable of binding to an androgen receptor of said cell, said steroid moiety being covalently linked to a polycationic salt having a pharmaceutically acceptable counterion, wherein said nucleic acid comprises detectably labelled nucleic acid, and detecting the presence of such labelled nucleic acid.

23. The complex of claim 1 wherein said nucleic acid comprises DNA encoding a p53 tumor suppressor.

24. The complex of claim 1 wherein said nucleic acid comprises DNA encoding a RB tumor suppressor.

25. The complex of claim 1 wherein said nucleic acid comprises DNA encoding a p16 tumor suppressor.

* * * * *

UNITED STATES PATENT AND TRADEMARK OFFICE
CERTIFICATE OF CORRECTION

PATENT NO.    : 6,468,981 B1
DATED         : October 22, 2002
INVENTOR(S)   : Petros and Liotta It is certified that error appears in the above-identified patent and that said Letters Patent is hereby corrected as shown below:

Column 2,
Line 41, delete "hepaitocytes" and replace with -- hepatocytes --.

Column 3,
Line 23, delete "91/1773" and replace with -- 91/17773 --.

Column 4,
Line 50, delete "completing" and replace with -- complexing --.

Column 5,
Line 22, delete "completed" and replace with -- complexed --.
Line 45, in the structure, delete the double bond between the 5-6 carbons and replace with a single bond.

Column 8,
Line 27, delete " $10^6$ " and replace with -- $10^{-6}$ --.
Line 30, delete " $10^6$ " and replace with -- $10^{-6}$ --.
Line 31, delete " 10-6" and replace with -- $10^{-6}$ --.

Column 9,
Line 66, delete "nudemice" and replace with -- nude mice --.

Column 11,
Line 24, delete "methyl nenolone" and replace with -- methyltrienolone --.

Signed and Sealed this

Eighteenth Day of February, 2003

JAMES E. ROGAN
*Director of the United States Patent and Trademark Office*